United States Patent [19]

Sisti et al.

[11] 4,403,520

[45] Sep. 13, 1983

[54] CONTROL VALVE FOR A DIRECT ON-COLUMN INJECTOR AND INJECTION METHOD

[75] Inventors: Giorgio Sisti, Melzo; Bruno Tosi, Carate Brianza, both of Italy; Sorin Trestianu, Brussels, Belgium; Mario Galli, Legnano, Italy

[73] Assignee: Carlo Erba Strumentazione S.p.A., Italy

[21] Appl. No.: 221,304

[22] Filed: Dec. 30, 1980

[30] Foreign Application Priority Data

Jan. 2, 1980 [IT] Italy ............................ 19005 A/80

[51] Int. Cl.³ .......................................... G01N 31/04
[52] U.S. Cl. ................................. 73/864.81; 73/23.1; 73/864.73
[58] Field of Search ........... 73/864.81, 864.73, 864.85, 73/864.87, 864.83, 23.1

[56] References Cited

U.S. PATENT DOCUMENTS

| | | | |
|---|---|---|---|
| 3,220,246 | 11/1965 | Barnum | 73/53 |
| 3,253,455 | 5/1966 | Ferrin | 73/864.84 X |
| 3,327,520 | 6/1967 | Stapp, Jr. | 73/23.1 |
| 3,458,699 | 7/1969 | Padita | 222/541 X |
| 3,675,466 | 7/1972 | Linenberg | 73/23.1 X |
| 3,733,909 | 5/1973 | Golowistikow | 73/864.85 X |
| 3,961,534 | 6/1976 | Gundelfinger | 73/864.84 |
| 3,985,016 | 10/1976 | Haruki | 73/23.1 |
| 3,985,066 | 10/1976 | Haruki | 73/23.1 |
| 4,068,528 | 1/1978 | Gundelfinger | 73/864.84 |
| 4,128,008 | 12/1978 | Linenberg | 73/864.81 |
| 4,165,644 | 8/1979 | Brandt et al. | 73/864.83 |
| 4,182,184 | 1/1980 | Bakalyar et al. | 73/864.87 |

FOREIGN PATENT DOCUMENTS

| | | | |
|---|---|---|---|
| 1698191 | 12/1971 | Fed. Rep. of Germany | 73/864.81 |
| 2211744 | 9/1973 | Fed. Rep. of Germany | 73/864.85 X |
| 135419 | 8/1978 | Fed. Rep. of Germany | 73/864.81 |
| 1388466 | 4/1963 | France | 73/864.81 |
| 2138486 | 1/1973 | France | 73/864.81 |
| 2447032 | 8/1980 | France | 73/864.81 |
| 19361 | 7/1980 | Italy | 73/864.81 |
| 1427821 | 3/1976 | United Kingdom | 73/864.2 |
| 1462391 | 1/1977 | United Kingdom | 73/864.81 |

Primary Examiner—Daniel M. Yasich
Attorney, Agent, or Firm—Lerner, David, Littenberg, Krumholz & Mentlik

[57] ABSTRACT

An apparatus for controlling the injection passage of on-column injector is disclosed. The apparatus includes a valve having at least one channel inside it and leading to the injection passage for the injection syringe needle. The channel is connected outside the injector to a source for carrier gas introduction, when the valve is open, or to the atmosphere, when the valve is closed, so as to allow a quick-type injection without the drawbacks of this injection type, as well as to have a solvent exhaust after injection.

11 Claims, 11 Drawing Figures

CONTROL VALVE FOR A DIRECT ON-COLUMN INJECTOR AND INJECTION METHOD

BACKGROUND OF THE INVENTION

1. Field of the Invention

This invention relates to a control valve for controlling injection passage of a direct on column injector, of the type having a valve body capable of rotating in a seat, to respectively open and close on injector passage for the injection needle insertion by means of a diametral through-channel, provided inside the valve body.

2. Description of the Prior Art

Valves of the mentioned type are applied to direct on column injectors as it is well known in the art. However in some cases, the use of direct injectors equipped with valves of the mentioned type, which are open during injection and closed at the end thereof leads to drawbacks, specially due to sample discrimination and loss of a sample portion.

In particular, when a so-called slow injection is carried-out, i.e. when the syringe piston is slowly lowered after the needle introduction into the injector, with open valve, the formation of a sample liquid cap may occur in correspondence with the free end of the injection needle, specially when the capillary column is at low temperature in correspondence to the injection zone. This liquid cap formation depends on different factors, among which solvent nature, column diameter and surface treatment of the glass forming the column itself, temperature of the injection zone, pressure and flow rate of carrier gas and amount of sample injected, of course together with injection speed. The introduction of carrier, which is performed upstream the zone of cap formation, causes a breaking of same, but a portion of the sample still remains on the needle tip. This sample portion is then drawn with the syringe outside the column, or may possibly remain inside the injector body, but in any case said portion, which is usually richer in heavy compounds, causes a discrimination of the sample, as the volatile components thereof are vaporized more quickly than the heavy ones during the needle insertion.

To overcome this drawback, it has been proposed to perform a quick injection, during which the syringe piston is quickly lowered. In this case, specially if the upstream end section of the column is heated, a vaporization zone in expansion and at high pressure is immediately formed downstream the needle tip, said zone tending to backwardly push the injected sample, inside the needle and above all into the passage between the needle and the column internal surface as well as into the injector passage. This involves, on one side, a backward ejection of small drops and vapour and, on the other side, a discrimination of heavy compounds inside the needle. Actually, vapours of volatile compounds and small drops of sample are produced, which are discharged in the atmosphere through the inlet passage for the syringe needle, as well as small drops which remain attached to the walls of the injector and of the initial section of the column, together with condensed vapours, with loss of the sample portion entrapped inside the injector body.

Another problem arising in the case of a direct on column injection, specially using certain solvents, is the problem of improving the work conditions at the injection end, by maintaining a certain exhaust to the atmosphere, in order to perform washing of the column and injector upper sections, as suggested by Grob. This exhaust is useful in some cases and Grob suggests to perform the same by keeping at least partially open the injection valve. However, this solution depends on the skill and sensibility of the operator, who not always proves to be up to the task.

SUMMARY OF THE INVENTION

An object of this invention is to provide a new control valve for the injection passage in a direct on column injector, which jointly or alternatively allows, to solve said problems to perform an injection without sample loss and without sample discrimination even in case of quick injection, on one side, and on the other side, to perform an exhaust at the injection end, without the necessity of controlling said exhaust operation in its entity, by a particular position of the valve opening.

Another object of the present invention is to provide a new quick-type injection method which can be carried-out even with columns at high temperature and allows to perform said injection without the sample loss and discrimination, as noticed in injections under the same conditions with known injectors, said method using a control valve according to the invention.

Said valve according to the invention essentially comprises at least one channel leading to the insertion passage for the injection needle and pneumatically connected to the passage itself in at least one of the valve positions, said channel being able to be connected, outside the injector, to a source of carrier gas or to the atmosphere. In particular, the valve body shows at least one channel which may be connected to the outside in the shown way, namely to the carrier gas supply when the valve is open and/or to the atmosphere when the valve is closed.

In other words, according to the invention, a valve for a direct on column injector is proposed, which allows, under the operator's control and according to the existing work conditions, to perform the mentioned exhaust with the valve in closed position and at the end of injection, as well as to carry out an introduction of carrier gas in correspondence to the valve during injection, these two operations being performed or excluded during one single injection, according to the requirements.

The introduction of carrier gas in correspondence to the valve during injection allows when the flow rate and pressure features of this introduction are suitably controlled, to eliminate all the above mentioned disadvantages in case of quick injections, in that the carrier gas flow gives rise to counterpressure which prevents sample loss and sample discrimination which usually occur with quick injection, as previously described. In the same way, the exhaust channel provided in correspondence of the valve allows to perform washing of the injector under the best possible conditions, in that said exhaust channel is positioned in the upper possible section.

DESCRIPTION OF THE PREFERRED EMBODIMENTS

Figure 1:
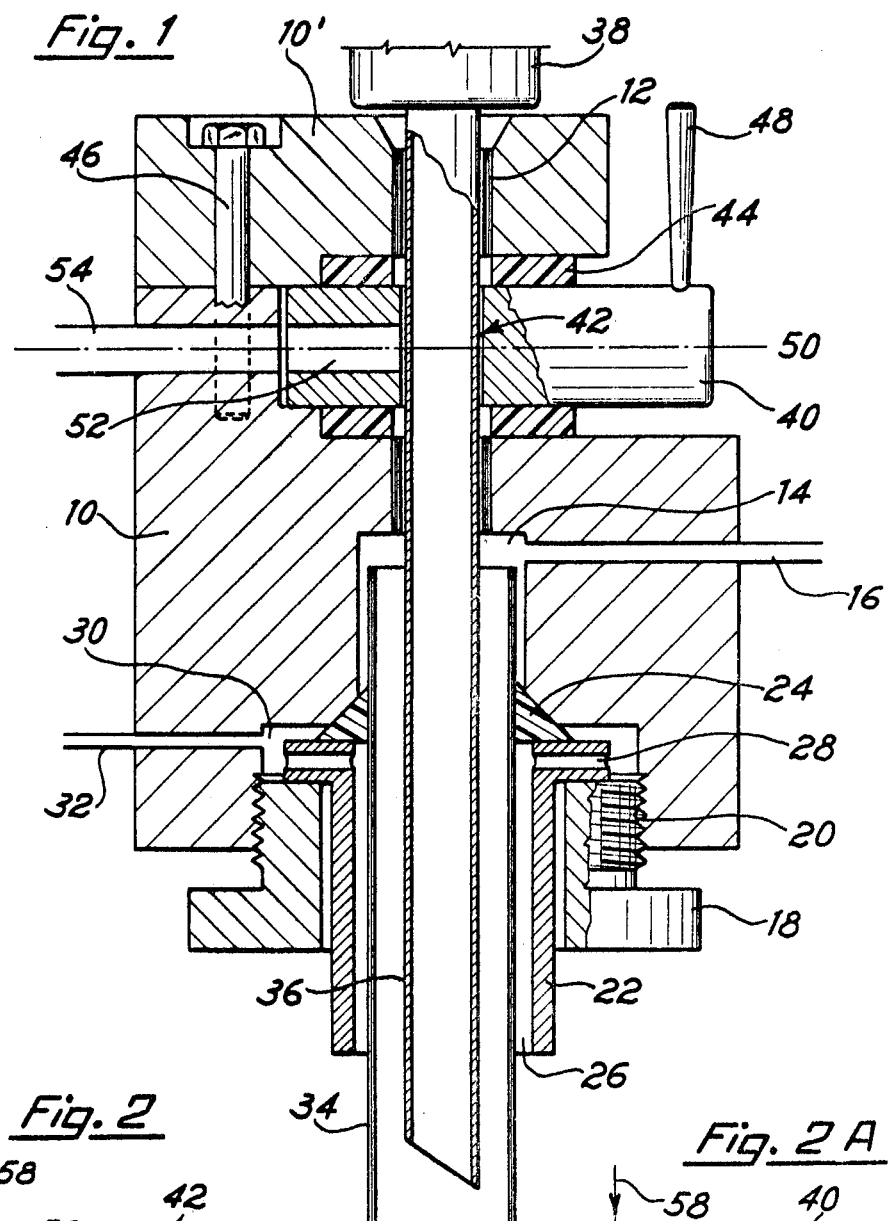
FIG. 1 is an axial cross-sectional view of a direct on column injector of the type with control valve according to the invention, in the valve open position.

With reference to FIG. 1, a direct on column injector of a type known in itself is essentially formed by an injector body 10 made of suitable metal material, inside which an injection passage 12 is provided having a jacket formed by a stainless steel tube, for instance with inner diameter of 0.28 mm, said injection passage 12 leading to a wider passage 14 forming a chamber to receive a carrier gas which is introduced through a duct 16 provided for in the injector body.

A nut 18 threaded in 20 fits to the base section of the injector body 10 and keeps in position a cooling jacket 22 and a trapezoidal sealing gasket 24, said cooling jacket 22 showing a central passage 26 connected by means of fittings 28 to a chamber 30 formed in the lower section of the injector and connected, through a duct 32, to an inlet of cooling auxiliary air. The gasket 24 pneumatically adheres to a glass capillary column 34, having for instance an inner diameter of 0.3 mm, which penetrates with its free end into the chamber 14.

The needle 36 of an injection syringe 38 is introduced through the injection passage 12 and the initial section of the gas chromatographic column 34, said needle having for istance an outer diameter of 0.23 mm.

Along the injection passage 12 a valve is positioned said valve, comprising a valve body 40 having a diametral through-channel 42, which is aligned with the injection passage in the valve open position. The valve body 40 is sealingly assembled, by means of gaskets 44, to the injector body 10, said gaskets, for instance made of polytetrafluoroethylene, being kept under pressure for instance by means of a series of bolts 46 acting on an upper section 10' of the injector body. The valve body 40 is controlled by means of a manual lever 48 which allows to perform a rotation of same around its own axis 50 until injection passage 12 is completely closed, in a substantially known way.

According to the invention, the valve body 40 shows another channel, for instance an axial duct 52 which, in at least one of the valve positions, is connected, through a passage 54 provided in the injector body 10, to the outside of the injector itself, where it can be connected, according to different cases and choices, to a source for carrier gas introduction as well as directly to the atmosphere.

For the application of the method of quick injection according to the invention, said passage or duct 54 is connected to the carrier gas source in the open position of valve body 40 and the conditions for carrier gas introduction are such as to create a counterpressure sufficient to avoid sample loss and sample discrimination by return on the outside of the injection needle 36. Alternatively or jointly, the duct 54 may be connected to the atmosphere when the valve body 40 is closed, in order to perform said exhaust as suggested by Grob.

Obviously, said injection conditions in a valve according to the invention can be achieved by positioning the channel 52, always inside the valve body in a different way form the one illustrated in FIG. 1 or by providing for more than one channel, to be connected with the outside.

Figure 2:
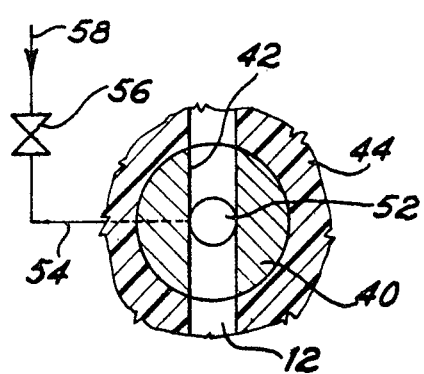
FIGS. 2, 2A, 3, 3A, 4, 4A, 5, 5A, 6 and 6A illustrate, in a sectional view in a plane perpendicular to the rotation axis of valve body, different possible solutions of a valve according to the invention, in the open and closed position respectively of the passage for the syringe needle introduction.
Figure 2A:
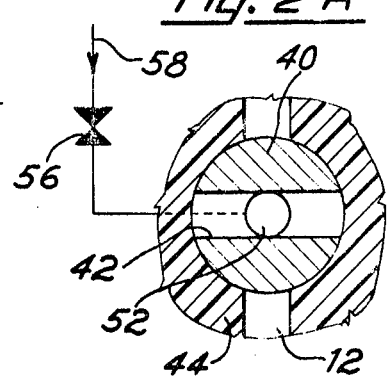

For example, in FIG. 2, the valve body 40 shows, besides the injection channel 42, an axial duct 52 similar to the one illustrated in FIG. 1, which is permanently in communication with a passage 54 connected by means of a valve 56 to a carrier gas source 58. In the condition of FIG. 2, the valve 40 is open and the channel 42 allows the passage of the injection syringe needle, and the valve 56 is correspondingly open to perform a simultaneous introduction of carrier gas under suitable conditions of pressure and flow rate. In FIG. 2A, the valve body 40 has been rotated by 90° and the injection passage 12 is closed, while simultaneously the valve 56 is closed, and therefore the duct 52 is no longer connected with the outside. Obviously in this case no exhaust occurs at the end of injection.

Figure 3:
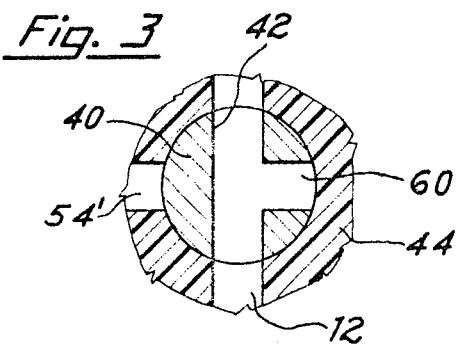
Figure 3A:
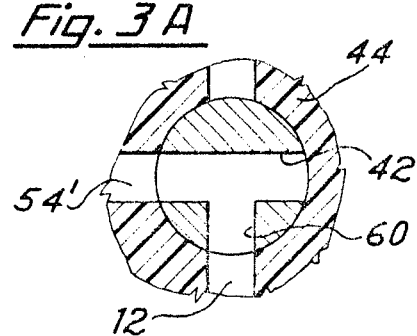

FIGS. 3 and 3A illustrate a valve to be used only to perform exhaust at the end of injection. In this case, the valve body 40 presents, besides the diametral through-channel 42, a radial duct 60 which, with the valve in its open position, as illustrated in FIG. 3, is closed by gaskets 44. When the valve is closed, as illustrated in FIG. 3A, the radial duct 60 is in connection with the downstream section of the injection passage 12 and said injection passage may exhaust towards the atmosphere through a passage 54' and through the diametral channel 42, which has been rotated of 90° so as to close the upper section of injection passage 12.

Figure 4:
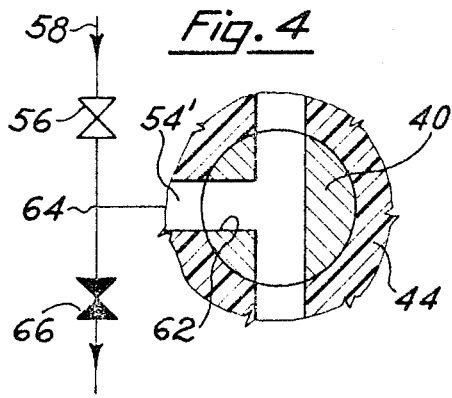
Figure 4A:
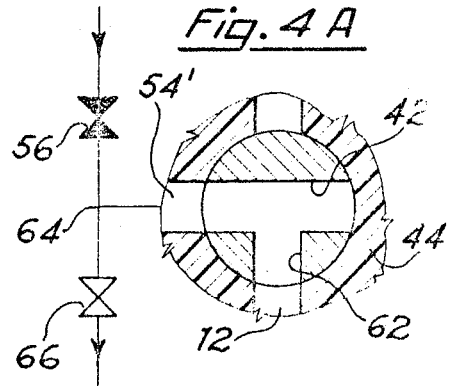

The embodiment of FIGS. 4 and 4A too, only uses one radial channel 62, 180° oriented with respect to the radial channel 60 of the previous figures and in connection to the passage 54' when the valve is in its open position (FIG. 4), while when the valve is in its closed position, said radial channel 62 connects the downstream section of injection passage 12 to the passage 54' through the diametral channel 42. The passage 54' is connected, outside the injector, to a T-fitting 64, the two branches of which lead, on one side, to a control valve 56 for introduction of carrier gas coming from a source 58, the valve 56 remaining open when the main valve 40 is open, as indicated in FIG. 4, and, on the other side, to a valve 66 which controls the connection to the atmosphere, said valve 66 being closed when the valve 40 is open. In the closed position of valve 40 (FIG. 4A), valve 56 is closed and valve 66 is open. In this case, it is possible to obtain both an introduction of carrier gas in the open position of valve body 40, and an exhaust towards the atmosphere in the closed position of said valve body 40.

Figure 5:
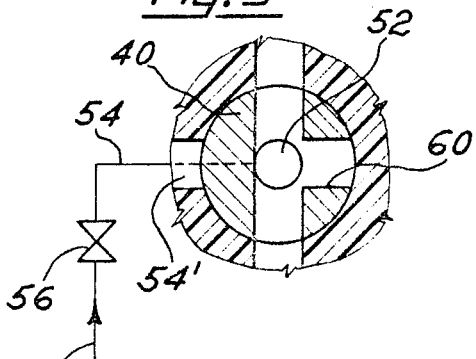
Figure 5A:
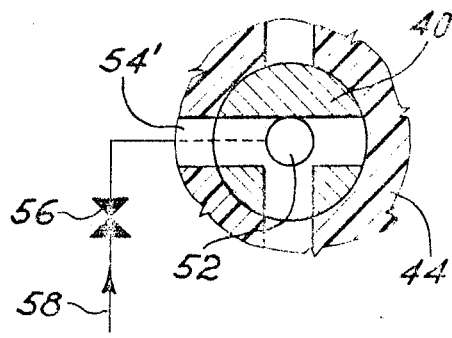

This double possibility of carrier gas introduction and exhaust towards the atmosphere may be achieved by means of two channels provided in the valve body 40, a duct 52 operating as in the case of FIGS. 2 and 2A and a radial duct 60 respectively operating as in the case of FIGS. 3 and 3A, the configuration being then that shown in FIGS. 5 and 5A.

Figure 6:
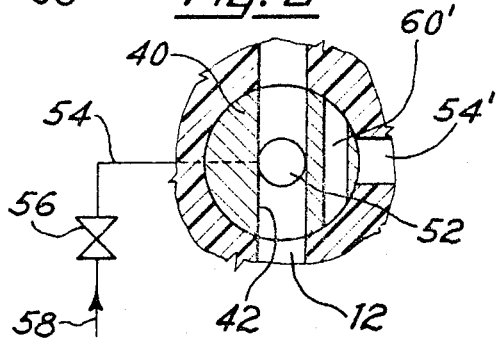
Figure 6A:
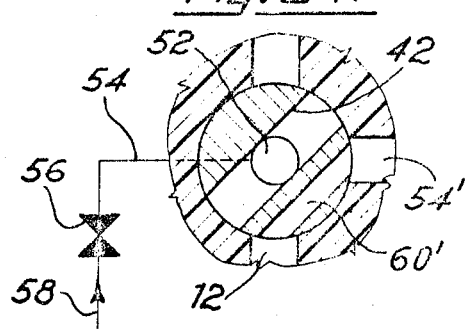

Finally, FIGS. 6 and 6A illustrate a further possible configuration, where the carrier gas introduction is performed by means of a channel 52 operating as in FIGS. 2, 2A and 5, 5A, while the exhaust is carried out through a duct 60', parallel to the passage 42 and connecting the injection passage 12 to the exhaust channel 54' when the valve is closed, said valve closure occurring by a rotation of less than 90°, for instance of 60° starting from the closure position.

Obviously the invention must not be considered as limited to the described and shown embodiments, but it may undergo to numerous modifications without departing from the spirit and scope of the present invention.

What is claimed is:

1. Apparatus for controlling the injection passage of an on-column injector, said apparatus comprising an injection body, said injection body having an injection passage therethrough for introduction of a sample to a gas chromatography column via an injection syringe inserted through said injection passage; a valve in said injection passage between the outside environment and the end of said injection passage; a second passage fluidically connected to said injection passage at the end of said injection passage; and means for introducing carrier gas into said second passage; wherein said valve includes a valve body with a through-channel, said valve selectively allowing insertion of an injection syringe needle through said through channel of said valve body and said injection passage when said valve is in its open position, wherein said valve also includes at least one second channel fluidically connected to said through-channel at one end and adapted to be connected to a source of carrier gas and/or to the atmosphere on the other end, and wherein said second passage is of a larger cross-sectional area than the cross-sectional area of the annular space created between said injection passage and said injection needle and/or between said through-channel and said injection needle when the injection needle is in its insertion position in said injection passage such that, when the carrier gas is passed through said second channel, the carrier gas introduced through said second channel will create a counter-pressure in said through-channel and said injection passage to avoid sample return through said through-channel and said injection passage without substantial increase in carrier gas flowing into said column.

2. Apparatus according to claim 1, wherein said at least one second channel is permanently connected to the injection passage and is controlled, outside the injector, by valve means which controls its connection to the carrier gas source or to the atmosphere, or which closes the passage itself.

3. Apparatus according to claim 1, wherein said at least one second channel is provided inside the valve body.

4. Apparatus according to claim 3, wherein said second channel is substantially coaxial to the rotation axis of the valve body and perpendicular to said through-channel, and wherein said second channel is connected to an external carrier gas source.

5. Apparatus according to claim 4, further comprising, between said carrier gas source and said coaxial channel, at least one control valve for carrier gas flow.

6. Apparatus according to claim 3 or 4, wherein the valve body has a channel parallel to said through-channel, which parallel channel is capable of connecting the injection passage by means of a fitting to the external atmosphere, when the valve is in its closed position, as obtained by rotating the valve body by an angle less than 90° from the open position.

7. Apparatus according to claim 3, wherein said valve body has a radial duct which leads radially from said through-channel and is connected to the injection passage when the valve is in its closed position.

8. Apparatus according to claim 7, wherein the valve has an atmosphere duct, which is connected to the injection passage through the through-channel and radial duct of the valve body when the valve is in its closed position, said atmosphere duct and said radial duct being closed when the valve is in its open position.

9. Apparatus according to claim 5 or 8, wherein said valve body has two channels, an axial and a radial channel respectively, wherein the axial channel is capable of being connected, through at least one second valve, to a carrier gas source for carrier introduction when the valve is in its open position and wherein the radial channel is capable of being connected to the atmosphere through a fitting in the valve seat when the valve is in its closed position.

10. Apparatus according to claim 7, wherein the valve has an outside connection duct which is connected to the injection passage through the radial duct and said through-channel when the valve is in its open position and respectively through the through-channel and radial duct when the valve is in its closed position, said outside connection duct being able to be connected through valve means to a carrier gas source or to the atmosphere.

11. A method for rapid on-column injection of a sample into a gas chromatographic apparatus having an injection body with an injection passage therethrough, having a valve in the injection passage, said valve including a through-channel so that, when the valve is in its open position, the through-channel is in alignment with the injection passage so as to allow insertion of an injection needle through the injection passage and the through-channel, and having a gas chromatographic column aligned with the injection passage so that, when an injection needle is inserted through the injection passage and the through-channel when the valve is in its open position, the end of the injection needle can be positioned in the gas chromatographic column so as to allow on-column injection of a sample from the injection needle, said method comprising the steps of inserting the injection end of a syringe needle through the injection passage and through the through-channel of the valve in said injection passage and into said column when the valve is in its open position; introducing carrier gas into the area between the syringe needle and the injection passage through separate channel in said valve during the time the valve is in its open position so as to create a counter-pressure sufficient to avoid sample return in the area between said syringe needle and said injection passage; and injecting the sample from the injection needle into the gas chromatographic column.

* * * * *